United States Patent [19]

Lenke et al.

[11] 3,997,614

[45] Dec. 14, 1976

[54] POLYTHIAFORMALS

[75] Inventors: Gerd M. Lenke, Dover, Del.; Kent B. McReynolds, Telford, Pa.

[73] Assignee: Reichhold Chemicals, Inc., White Plains, N.Y.

[22] Filed: Dec. 6, 1974

[21] Appl. No.: 530,267

Related U.S. Application Data

[63] Continuation-in-part of Ser. No. 300,685, Oct. 25, 1972, abandoned.

[52] U.S. Cl. .................. 260/609 R; 260/30.8 R; 260/761; 260/609 F
[51] Int. Cl.$^2$ .................. C07C 149/14
[58] Field of Search .......... 260/609 R, 30.8 R, 761

[56] References Cited

UNITED STATES PATENTS

| | | | |
|---|---|---|---|
| 2,668,862 | 2/1954 | Price | 260/609 R |
| 2,905,720 | 9/1959 | Benneville et al. | 260/609 R |
| 2,905,721 | 9/1959 | Benneville et al. | 260/609 R |
| 3,005,853 | 10/1961 | Wilgus et al. | 260/609 R |
| 3,290,382 | 12/1966 | Hubscher | 260/609 R |
| 3,446,775 | 5/1969 | Bertozzi et al. | 260/609 R |
| 3,503,930 | 3/1970 | Morris et al. | 260/609 R |
| 3,635,736 | 1/1972 | Oftedahl | 260/609 R |

OTHER PUBLICATIONS

Lienhard et al.; J. Am. Chem. Soc. 88, pp. 3982–3995 (1966).
Walker; "Formaldehyde" (1963), pp. 279–280.

*Primary Examiner*—Lewis Gotts
*Assistant Examiner*—D. R. Phillips

[57] ABSTRACT

Water-insoluble polythiaformals having substantial antioxidant activity are produced by the liquid phase reaction of primary thiadiols with formaldehyde and mono-alcohol in the presence of an acid catalyst.

10 Claims, No Drawings

POLYTHIAFORMALS

CROSS-REFERENCE TO RELATED APPLICATIONS

This application is a continuation-in-part of application Ser. No. 300,685 entitled "Novel Plasticizer Compositions and Method for Their Preparation," filed on Oct. 25, 1972, now abandoned.

BACKGROUND OF THE INVENTION

This invention relates to new compositions of matter which are useful as plasticizers for polymeric materials. More particularly, this invention relates to a novel class of polymers which are capable of plasticizing a wide variety of both natural and synthetic polymers.

Plasticizers are an important adjunct to the utilization of polymeric materials in that they are widely incorporated in both natural and synthetic polymers to increase the workability, flexibility or distensibility of such materials. In addition, they are often used as extenders for polymeric materials. In the plasticization or extension of polymers, organic plasticizers are generally used which are usually moderately high molecular weight liquids or, occasionally, low-melting solids.

Though there is considerable debate as to the mechanism by which various plasticizers function, most plasticizers for polymeric materials are of the solvent type, i.e. rather high boiling, normally liquid organic compounds which are chemically inert toward the polymers in which they are used, but in which the polymer swells or is at least partially soluble and will therefore be readily softened by intimate contact with the plasticizer. The most widely used solvent-type plasticizers include esters of carboxylic acids or phosphoric acid, hydrocarbons, halogenated hydrocarbons, ethers, glycols and sulfonamides.

In the selection of a plasticizer, it is of particular importance that the plasticizer exercise the effect for which it is intended without undue adverse effect on other properties of the polymer and that it be at least comparable in cost and preferably lower in cost than the polymer to which it is added.

A particular problem in the field of plasticization has been the plasticization of polymeric materials which are to be exposed to high temperatures under oxidative conditions. Plasticizers for this application must be non-volatile, must be compatible with the base polymer and must maintain the flexibility of the polymer and preferably have antioxidant activity, all of which must be done without significant impairment of the other performance properties of the polymeric material.

A new class of plasticizers has been discovered which not only have the above-described capabilities to plasticize high temperature performance polymers, but also to improve the resistance of such polymers to oxidative deterioration. Furthermore, these plasticizers, which possess the versatility to plasticize and otherwise improve the properties of many polymeric materials, have exceptional resistance to hydrolysis.

DISCUSSION OF THE PRIOR ART

In U.S. Pat. No. 2,785,947, Kress and Abrams disclose the use of polyacetals of monoaldehydes and dialdehydes containing up to 8 carbon atoms to treat fabrics and thus improve their laundry and dry cleaning durability. The disclosed polyacetals are water-soluble. Kress in U.S. Pat. No. 2,785,949 discloses the use of polyacetals like those from U.S. Pat. No. 2,785,947 as substitutes for melamine resins to give dimensional stability to cellulosic textile materials. In U.S. Pat. No. 2,785,995 to Kress, the same type of polymeric acetals are used to improve the wet strength of paper. Matuszak et al. in U.S. Pat. No. 2,796,401 disclose the use of complex formals prepared by reacting formaldehyde, mono-alcohols and polyhydric alcohols as a lubricant base. The polyformals disclosed are water-soluble. In U.S. Pat. No. 2,786,081 to Kress, the inventor discloses the use of water-soluble aldehyde/polyol condensation products as plasticizers "either of water-soluble or organic-soluble polymers." However, no example of such use is given. Cottle and Young, in U.S. Pat. No. 2,796,423, reveal the use of polyformals similar to those of U.S. Pat. No. 2,796,401 as synthetic lubricants. Mertzweiller, in U.S. Pat. No. 2,796,441, discloses the use of polyformals of formaldehyde and long chain mono-alcohols derived from the Oxo process as synthetic lubricants. In U.S. Pat. No. 2,838,573, Matuszak and Ready disclose the preparation of complex formal lubricants by reacting formals with a glycol. Johnson in U.S. Pat. No. 2,846,404 discloses the use of polyformals to inhibit foam in steam boilers. Kress again, in U.S. Pat. No. 2,878,294, discloses water-soluble polyacetals prepared by reacting polyalkylene glycol or thiodiglycol, monohydric alcohol and aldehydes, which products are said to be useful as hydraulic fluids. However, no examples are set forth in Kress that show the reaction of the thiodiglycol.

The above described polyformals of the prior art would not be operable as plasticizers for polymers such as nitrile and chloroprene rubbers because they are substantially incompatible therewith. Moreover, they would not enhance the heat and oxidation resistance of polymers, to which they were added, since they contain no component or functional group capable of taking part in an anti-oxidative chemical reaction.

Thus, while the prior art teaches much about the composition and properties of water soluble polyformals, the properties and various uses therefrom, there is no suggestion of the unique properties and uses of the water insoluble plasticizer compositions of the invention.

BRIEF DESCRIPTION OF THE INVENTION

This new class of plasticizers, which may be broadly characterized structurally as polythiaformals, is represented by the following chemical structure:

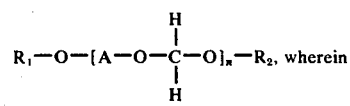

$R_1$ is selected from the group consisting of hydrogen and the monovalent group

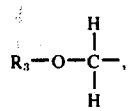

$R_2$ and $R_3$ are independently selected from the group consisting of hydrogen and monovalent residues of mono-alcohols and of thiadiols, A is the divalent residue of a thiadiol, and $n$ is an integer from 1 through 40.

Compounds of the above general formula, which are a unique class of polythiaformals, may be prepared by the liquid phase reaction of a primary thiadiol and formaldehyde, either with or without a mono-alcohol, in the presence of an acid catalyst. When the reaction is conducted in the absence of the mono-alcohol, the resultant polymer contains terminal hydroxy groups. On the other hand, when the reaction is conducted in the presence of the mono-alcohol, at least a portion of the terminal hemiformal groups undergo a condensation reaction with the mono-alcohol by which the polymer is "endcapped" with the mono-alcohol residue. Endcapping of this nature can be carried out simultaneously with or after formation of polythiaformals structure.

It has been found that useful new endcapped compositions of matter are produced when the monovalent residues of mono-alcohols are present in the statistically average polymer chain at least to the extent of 20 mole percent of the terminal groups.

DEFINITIONS

Within the context of the invention, various terms used herein have the following special meanings:

"Mono-alcohol residue" refers to the monovalent moiety, which would result from exclusion of the hydroxy group from a mono-alcohol. The term does not imply, nor is it limited to any particular reaction mechanism.

"Thiadiol" refers to thiaalcohols having at least 2 but not more than 6 hydroxy groups, at least 1 of which groups is of primary configuration.

"Thiadiol residue" refers to the monovalent or divalent moiety, which would result from exclusion of one or more hydroxy groups from a thiadiol. The term does not imply, nor is it limited to any particular reaction mechanism.

The term "thia-" implies that at least one monosulfur linkage exists in the molecule between two adjacent carbon atoms, which configuration is often referred to as a thioether linkage.

"Protonic acid" denotes acids which, in an appropriate solvent, such as water, having a high dielectric constant are capable of dissociation into a proton and an anion and which have a dissociation constant of at least $1 \times 10^{-5}$ and preferably at least $1 \times 10^{-2}$ (measured in water).

"Activator" refers to metal oxides of a metal of Group IIA and/or IIB of the periodic system of elements.

COMPONENTS OF THE REACTION MIXTURE

Typical classes of primary thiadiols comprise dihydroxy terminated substituted and unsubstituted thiaalkylenes, oxathiaalkylenes, polythiaalkylenes, poly(oxa-thia) alkylenes, oxa-poly(thiaalkylenes), thiapoly(oxa-alkylenes) and carboxythiaalkylenes.

The following are specified examples of primary thiadiols, which may be used to make the polythiaformal compositions of the invention:

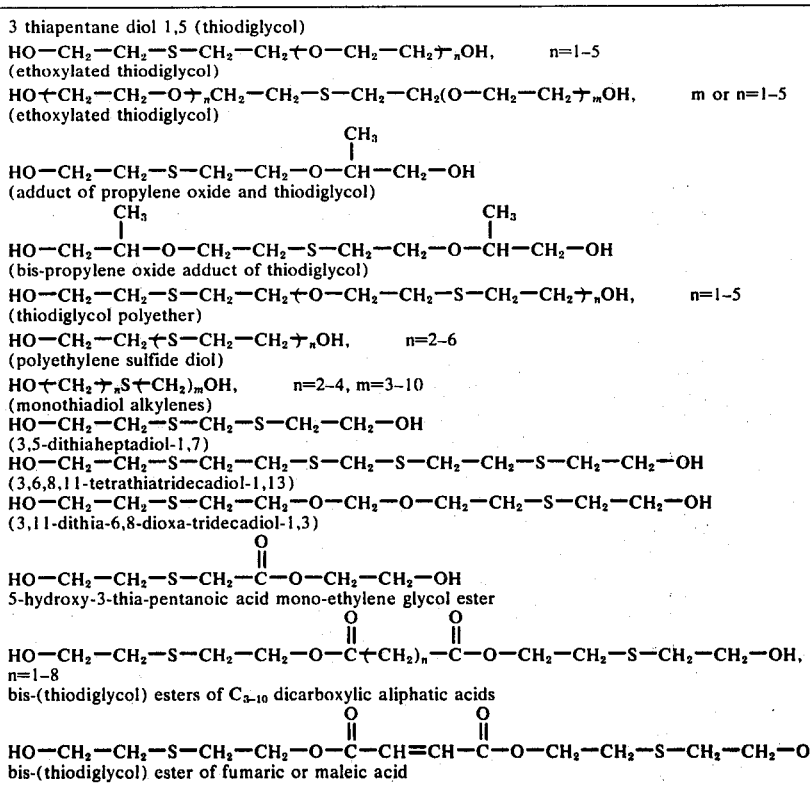

It is preferred to employ primary diols in synthesizing the compositions of the invention, because of the tendency of secondary alcohols to undergo undesirable side reactions.

Furthermore, it is possible to employ in the invention mixtures of primary thiadiols with other diols or polyols, i.e. diols or polyols which do not contain thioether linkages, so long as such diols or polyols do not comprise more than about 60 percent of the total weight of thiadiol and diol and/or polyol.

Examples of suitable non-sulfur-containing polyols, to be used only in admixture with at least equal amounts by weight of thiadiols, include the following:
ethylene glycol (1,2-ethanediol)
poly(ethyleneoxide) glycols, (e.g. diethylene glycol, triethylene glycol etc.)
1,3-propanediol
1,2-propanediol
1,2,3-propanetriol
1,4-butane diol
2-methyl-1,3-propanediol
1,5-pentanediol
3,3-dimethyl-1,3-propanediol pentaerythritol
1,6-hexanediol
2-ethyl-1,6-hexanediol
1,4-dimethylol-cyclohexane
1,4-dimethylol-benzene Although it is known that 1,2- and 1,3-diols, such as ethylene glycol and 1,3-propanediol, readily form 1,2-dioxolane or 1,3-dioxane derivatives with formaldehyde, instead of long chain polymers, it is demonstrated by an embodiment of this invention that, e.g. ethylene glycol, can be used in combination with thiodiglycol to form a linear polyformal with both diols incorporated.

Formaldehyde rapidly reacts with the hydroxy groups of the mono-alcohol or diol to form non-volatile hemiformal compounds which then condense further to formal linked polymers. Water is produced in this reaction which could bind any free unconverted aldehyde to a non-volatile hydrate. It is preferred to use paraformaldehyde as a source of formaldehyde since it is relatively non-volatile but depolymerizes readily under reaction conditions. The free formaldehyde is almost instantly used up in the formation of hemiformal.

Mono-alcohols which may be used to endcap the hydroxy-terminated polythiaformals of the invention, include the following:
methanol
ethanol
1-propanol
1-butanol
1-pentanol
benzyl alcohol
n-butylglycol
isobutyl glycol
n-butyl diglycol
isobutyl diglycol n-butyl polyglycol
$C_4H_9\text{---}(O\text{---}CH_2\text{---}CH_2)_n\text{---}OH$, n=3 to 10

1-hexanol
1-heptanol
1-octanol
2-ethyl-hexanol-1
2-ethyl isohexanol
1-decanol
n-dodecanol-1
Neodol-23* (mixed $C_{12}/C_{13}$ primary alcohols)
Neodol-25* (mixed $C_{12}/C_{15}$ primary alcohols)
Neodol-45* (mixed $C_{14}/C_{15}$ primary alcohols)
ethyleneglycol monobutyrate
ethyleneglycol monolaurate
ethyleneglycol monostearate
allyl alcohol
crotonic alcohol
ethylthioethanol (3 thiapentanol) $CH_3\text{-}CH_2\text{-}S\text{-}CH_2\text{-}CH_2\text{-}OH$

*Tradename of Shell Chemical Co., Houston, Texas

Typically, mono-alcohols having from 6 through about 30 carbon atoms may be used in synthesizing the products of the invention. Aliphatic alcohols having from 8 to 16 carbon atoms are preferred, of which 2-ethyl-hexanol, n-dodecanol and tridecanol are especially preferred.

From the foregoing discussion of the mono-alcohols and thiadiols, which may be used, it will be apparent that the reactivity of the hydroxy groups thereof is an essential criterion of their suitability for synthesis of the plasticizers of the invention. Thus, it will be recognized that the residues of the mono-alcohols and thiadiols may vary considerably in structure, so long as the residual moiety does not interfere too greatly with the basic interactions of the hydroxy groups and/or the catalyst. The selection of particular mono-alcohols and thiadiols may be a means of "tailoring" the molecule for use in a given polymer matrix. By selecting mono-alcohols and thiadiols as to size (molecular weight), configuration and polarity, the products of the invention can be varied widely in compatibility, efficiency, permanence and solvent power for particular polymers.

Thus, the above-referred alcohol residues may be of either acyclic or cyclic configuration, as well as combinations thereof and include hetero atoms, such as sulfur, nitrogen and oxygen and substituent groups, such as halogen and carboxyl. The mono-alcohol residues include both substituted and unsubstituted alkyls, thiaalkyls, oxa-alkyls, alkaryls, aralkyls, alkenyls, aryls, heterocyclyls, heterocycloalkyls, carboxyalkyls and poly(alkylene-oxides) and mixtures thereof. Amine substituents, however, are to be avoided.

Protonic acids which may be used to catalyze the reaction of the diols with formaldehyde include hydrochloric acid, sulfuric acid, hydrobromic acid, chlorosulfonic acid, phosphoric acid, p-toluene-sulfonic acid, dodecyl benzene sulfonic acid and other strong organic acids, such as trichloroacetic and trifluoroacetic acids. Lewis acids such as $CaCl_2$, $AlCl_3$, $BF_3$ and $BF_3$ etherate may also be used to catalyze the reaction, since they are rendered protonic in the presence of the alcohol reactants or even small amounts of water in the reaction system, such as would result from the condensation reactions or might be present as an impurity in the starting materials. Strong organic acids, such as p-toluene sulfonic acid, dodecylbenzene sulfonic acid, methane sulfonic acid, trichloroacetic acid and trifluoroacetic acid, are preferred catalysts for the above-described reactions because of their solubility in both the aqueous and organic phases of the initial reaction mixture.

DESCRIPTION OF THE PROCESS

One advantage of the unique plasticizer compositions of the invention is that they are quite easy to synthesize and require only basic production equipment and moderate conditions of reaction pressure and temperature.

Basically, the method of synthesis is a single-step process in which all of the reaction components and the catalyst are charged at the start of the reaction. However, the endcapping may be performed after reaction between the diol and the formaldehyde has been completed.

The process is carried out as a bulk liquid phase reaction, in which at least one of the reactants is a liquid and is capable of acting as a dispersing medium for the other reactants. Thus, while any of the reactants may be normally solids, they nevertheless must be dispersible in the liquid reactant medium and be reactive when so dispersed. Consequently, the reactants useful in the practice of the invention must be dispersible in the reaction mixture in at least one of the following ways: (1) solubility in at least one other reactant which is liquid; (2) non-solution dispersibility in at least one other reactant which is liquid; (3) solvency for at least one other reactant; and (4) constitution as a liquid phase in which at least one insoluble reactant is dispersible.

In most instances, the diol is liquid at reaction conditions and the other reactants — whether liquids or solids — are soluble therein. One notable exception is paraformaldehyde, which is insoluble in the reaction system, but upon dispersion therein is depolymerized by the presence of the catalyst to formaldehyde gas, which almost instantly takes part in the formation of a hemiformal, as discussed hereinabove.

The process is not particularly sensitive to reaction conditions and requires only modest heating to about 60° C to obtain adequate reaction rates. However, temperatures of at least about 90° C are preferred further to speed the reaction and also to facilitate separation of water formed during the reaction. Since water is formed by reaction of the formaldehyde with the diol to form formal linkages, it is preferred to remove the water by stripping in order to shift the equilibrium of the reaction to favor formal formation. One molecule of water is formed for each formal bond. So far as is known the maximum reaction temperature is limited only by the volatility and/or thermal stability of the reactants and products therefrom, whichever may be controlling.

The synthesis of this new class of compounds is likewise not sensitive to pressure variations and may therefore be conducted at atmospheric pressures. Vacuum conditions may be useful in the latter stages of the reaction to remove water and other volatiles from the system.

The process can be carried out under air or an inert atmosphere, such as nitrogen or inert gas (essentially $N_2$ and $CO_2$). Inert atmospheric blanketing is ordinarily preferred because of safety considerations.

The end product of the reaction is comprised of a complex mixture of a polythiaformals conforming to the above discussed general structural formula. Normally the stripped product will be homogeneous. However, in instances where a water-immiscible monoalcohol is used, any unreacted alcohol or any alcohol which has reacted to a "monomeric" formal, excluding the diol, may form a separate liquid phase.

Water absorbing materials may also be used to remove reaction water from the product, e.g. $CaCl_2$, $CaSO_4$, $Al_2(SO_4)_3$, $Na_2SO_4$, $MgCl_2$, $MgSO_4$, NaCl, KCl, silica gel, molecular sieves and the like. In addition, hydrocarbon solvents may be admixed with the reaction mixture to form azeotropic mixtures with the reaction water, by which removal of the water by distillation can be facilitated, although, generally, the use of such stripping additives is not preferred. Examples of such solvents are benzene, toluene and xylene.

In some instances, it may be preferred to neutralize and/or remove the acidic catalyst residues upon completion of synthesis. This may be accomplished readily by means of the addition of an acid acceptor or preferably, a base. Suitable bases include NaOH, KOH, $Na_2CO_3$, $NaHCO_3$ and $K_2CO_3$ in powder, flake or pelletized form. Acid acceptors include molecular sieves, ion exchange resins, silicate polymers, aluminum oxides and the like.

Though the process is basically a single step process, it may be conducted with incremental addition of one or more of the reactants and/or may be conducted either batchwise or continuous.

Though it is contemplated that the plasticizers of the invention will have the greatest utility for the plasticization of nitrile and polychloroprene rubbers, it will, of course, be realized that they may be effective for plasticizing and/or extending other polymeric materials such as SBR, polybutadiene, polyvinyl acetate, polyvinyl chloride, polyvinylidene chloride, polystyrene, natural rubber and many other natural and synthetic polymers. It appears that the plasticizers of this invention are less suited for the plasticization of most substantially saturated all-hydrocarbon polymers, such as poly-$\alpha$-olefins, e.g. polyethylene, polypropylene, poly-n-butene, polyisobutene and copolymers thereof, including such elastomers known as EPM and EPDM.

Polymers of organic monomers which also contain atoms other than hydrogen and carbon are preferred. Exemplary of such monomers are carboxylic acids (acrylic and methacrylic acids, fumaric, maleic and itaconic acids), acrylic and methacrylic acid derivatives (acrylonitrile, methacrylonitrile, acrylamide, methacrylamide, N-methylolacrylamide), vinyl esters (vinyl acetate), vinyl ethers, vinyl ketones, and vinyl heterocyclic compounds (N-vinyl pyrrolidone and vinyl pyridines).

In the case of copolymers of $\alpha$-olefins with other copolymerizable monomers which are not $\alpha$-olefins, the compositions of the invention are more effective in their plasticization, when the $\alpha$-olefin content of such polymers is below about 80 mole percent and preferably below about 70 mole percent.

It will be realized by those skilled in the art that the plasticizers of the invention constitute a family of related polymers which have a wide variety of properties as to molecular weight, polarity, water solubility and molecular configuration. Thus, not every member of the family can be expected to provide the same effect to a particular polymer. However, by selection of molecular weight, endcapping agents and particular thiadiols, it will be recognized by those skilled in the art that the plasticizer compositions of the invention can be "tailor made" to accommodate a broad scope of polymers.

In general, the following technique for varying the properties of the plasticizer of the invention will apply. Polarity can be reduced by endcapping with the relatively less polar residue of a mono-alcohol, by which the number of highly polar terminal hydroxy groups is reduced. Molecular weight can be reduced by increasing the proportion of thiadiol vis-a-vis formaldehyde. Greater hydrophobicity can be imparted by the selection of endcapping alcohols having long chain alkyl groups and the degree of polarity can be reduced by regulating the extent of endcapping. Thus, the compositions of the invention can be made to possess selected degrees of compatibility for a wide variety of polymers, particularly those polymers, as mentioned above, which are not derived primarily from $\alpha$-olefins and which are not highly crystalline in character.

In the formulation of polymeric materials utilizing the plasticizers of the invention, the amount of plasticizer relative to the polymer can be varied over a wide range, depending, of course, upon (1) the character of the particular plasticizer; (2) the character of the polymer; (3) the type of modification which is sought for the polymer; and (4) the extent of polymer modification which is sought.

When the plasticizers of the present invention are employed in nitrile rubbers, i.e. copolymers of butadiene and acrylonitrile, and neoprene rubbers, i.e. polychloroprenes, it is a particular preferred embodiment that there also be present an activator. The presence of the activator in combination with the plasticizers imparts to such rubbers improved heat and oxidation resistance. Of course the degree to which such properties are imparted to the rubbers depends on the particular formulation and compounding thereof.

In the case of copolymers of butadiene and acrylonitrile, generally, the greatest improvement in heat and oxidation resistance has been observed when the activator used was zinc oxide, magnesium oxide, cadmium oxide or mixtures thereof. The most preferred activator is cadmium oxide, which seems to show the greatest effect. Typically the activator will be present in the range of from about 2 to 30 parts by weight based upon 100 parts of the polymer solids and preferably in the range of from about 3 to about 15 on the same weight basis. Moreover, to obtain optimum benefits of the plasticizers, it is important that they have an hydroxy content of at least about 1 meq. OH/g (determined by the Acetic Anhydride Method of C. L. Ogg, W. L. Porter, and C. O. Willits, Ind. Eng. Chem. Anal, Ed 17 pp 394-397 (1945)) and a number average molecular weight ($\overline{M}n$) of at least about 400.

The amount of plasticizer used in copolymers of butadiene and acrylonitrile may vary widely depending upon a number of factors, for instance the particular method used for polymerization and the exact composition of the polymer. Generally, however, the amount present will be in the range of from about 2 to about 40 parts per 100 parts of rubber and most preferably in the range of from about 5 to about 20 on the same weight basis.

In the case of neoprene rubbers, i.e., polychloroprene, the hydroxy content of the plasticizers should be below about 1 meq. OH/g. At higher hydroxy contents, the plasticizers will effect premature curing of the neoprene green stock. The number average molecular weight of the plasticizers used in neoprene rubbers should typically be in the range of from about 500 to about 2000 and preferably from about 700 to about 1500. The plasticizers may be present in amounts of from 5 to 50 and preferably from about 10 to about 30 parts per hundred rubber.

The invention will be better understood by reference to the following examples, in which all proportions are expressed in parts by weight unless otherwise indicated:

In expressing the hydroxy content of the present composition, it should be distinctly understood that the Acetic Anhydride Method of C. L. Ogg, W. L. Porter, and C. O. Willits Ind. Eng. Chem. Anal, Ed 17, pp. 394-397 (1945) was followed since a number of methods for obtaining hydroxy content are known in the art and the numerical values obtained will vary somewhat depending upon the exact method used.

EXAMPLE I

The synthesis of non-endcapped (hydroxy-terminated) products of the invention is illustrated by the following procedure in which the process was carried out in a nitrogen-purged glass reaction vessel equipped with a sealed mechanical stirrer, thermometer, reflux condenser, Dean-Stark trap and inlet and outlet means for the purge gas.

The above-described vessel was first charged with commercial grade thiodiglycol (TDG) and paraformaldehyde and about one-half of the intended charge of p-toluene sulfonic acid catalyst. The reaction vessel was then placed in a heating mantle and the first charge heated to 90°–110° C. After about one-half hour most of the dispersed paraformaldehyde was dissolved and some water had formed, indicating reaction between the TDG and formaldehyde. After about one hour, the remaining half of the p-toluene sulfonic acid catalyst was added and the reaction allowed to proceed.

After a total elapsed time of 4 hours, the reaction mixture was maintained at 100°–128° C to strip off the reaction water, which was collected in a Dean-Stark trap. Finally a moderate vacuum was applied, while heating the reaction mixture to 120°–140° C to remove the residual volatiles. The stripped reaction material was then cooled to room temperature.

The resulting product was a water-immiscible, light colored, low-to-medium viscosity liquid having a number average molecular weight ($\overline{M}n$) of 445 (as determined by vapor phase osometry).

The above-described procedure was repeated for eleven additional runs, including one run utilizing pilot-plant scale facilities. In the following runs various reactant charge proportions were utilized and the number average molecular weight ($\overline{M}n$) and hydroxyl content of the products determined, and compared to theoretical values in accordance with the following reaction mechanism:

$$(n+1) \; (HO-CH_2-CH_2-S-CH_2-CH_2OH) + nCH_2O \rightarrow$$
$$HO(CH_2-CH_2-S-CH_2-CH_2-O-CH_2-O)_nCH_2-CH_2-S-CH_2-CH_2OH + nH_2O$$

within the context of the general formula presented hereinabove, the symbolized groups thereof have the following compositions:

| Group | Composition |
|---|---|
| $R_1$ | hydrogen |
| $R_2$ | $-CH_2-CH_2-S-CH_2-CH_2-OH$ |
| A | $-CH_2-CH_2-S-CH_2-CH_2-$ |

The yields and compositions obtained compared quite favorably with the theoretical calculated values as is shown in Table I below:

TABLE I

Synthesis of Hydroxy-Terminated Polyformals - Comparison of Theoretical and Found Composition

| Run No. | Charge | | | Yield [2] | Molecular Weight ($\overline{Mn}$) | | meq. OH/g | | OH Groups per Molecule | |
|---|---|---|---|---|---|---|---|---|---|---|
| | Thiodi-glycol moles | Formal-dehyde moles | Catalyst [1] % by wt. | % by wt. | Theoretical | Found | Theoretical | Found | Theoretical | Found |
| 1 | 1 | 0.7 | 0.28 | 95 | 435 | 445 | 4.6 | 4.4 | 2 | 1.9+ |
| 2 | 1 | 0.75 | 0.28 | 87 | 520 | 580 | 3.8 | 3.3 | " | 1.9 |
| 3 | 1 | 0.8 | 0.27 | 94 | 660 | 605 | 3.0 | 3.3 | " | 2.0 |
| 4 | 1 | 0.9 | 0.27 | 89 | 1,330 | 970 | 1.5 | 2.1 | " | 2.0 |
| 5 | 2 | 1.4 | 0.28 | 98 | 435 | 435 | 4.6 | 4.1 | " | 1.8 |
| 6 | 4 | 2.8 | 0.44 | 97 | 435 | 485 | 4.6 | 4.0 | " | 1.9+ |
| 7 | 4 | 2.8 | 0.44 | 96 | 435 | 410 | 4.6 | 4.7 | " | 1.9 |
| 8 | 4 | 2.8 | 0.7 | 97 | 435 | 450 | 4.6 | 4.3 | " | 1.9+ |
| 9 | 380 | 266 | 0.29 | >95 | 435 | 410 | 4.6 | 5.3 | " | 2.2 |
| 10 | 2 | 1.6 | 0.27 | 99 | 660 | 725 | 3.0 | 2.9 | " | 2.1 |
| 11 | 2 | 1.6 | 0.27 | 98 | 660 | 580 | 3.0 | 3.0 | " | ca. 1.8 |
| 12 | 4 | 3.2 | 0.43 | 95 | 660 | 675 | 3.0 | 3.0 | " | 2.0 |

[1] p-Toluene sulfonic acid.
[2] Based on theoretical maximum yield after removal of all water generated in the condensation reaction.

The above data also indicate that changes in catalyst concentration do not have a noticeable effect on the character of the product produced by this process.

EXAMPLE II

In this example, a portion of the reaction product from Run No. 9 of the previous example was separated and further reacted in accordance with the procedure described in Example I by the addition of 3.2% by weight additional formaldehyde (added as paraformaldehyde) and 0.3% by weight p-toluene sulfonic acid catalyst. After 6 hours of additional reaction and stripping of the reaction water, a more viscous water immiscible liquid product was obtained, in which the molecular weight ($\overline{Mn}$) had been increased from 410 to 605 and the hydroxy content had decreased from 5.32 to 3.51 meq. OH/g. The number of hydroxy groups per molecule was essentially unchanged.

EXAMPLE III

Utilizing the basic procedure of Example I, another series of experiments was conducted, in which a number of polyformal products was prepared in the presence of 2-ethylhexanol. In this process the polyformals were partially terminated with this monoalcohol in accordance with the following reaction mechanism:

$$n(HO\text{-}CH_2\text{-}CH_2\text{-}S\text{-}CH_2\text{-}CH_2\text{-}OH) + nCH_2O + iso\text{-}C_8H_{17}OH \rightarrow C_8H_{17}\text{-}O\text{-}CH_2\text{-}O(CH_2\text{-}CH_2\text{-}S\text{-}CH_2\text{-}CH_2\text{-}O\text{-}CH_2\text{-}O)_{n-1}CH_2\text{-}CH_2\text{-}S\text{-}CH_2\text{-}CH_2OH + nH_2O$$

Within the context of the general formula for the products of the invention, the symbolized groups thereof have the following composition and values:

| Group | Composition |
|---|---|
| $R_1$ | 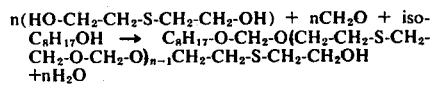 |
| $R_2$ | $-CH_2-CH_2-S-CH_2-CH_2-OH$ |
| $R_3$ | 2-ethylhexyl |
| A | $-CH_2-CH_2-S-CH_2-CH_2-$ |

The yields and compositions obtained again compared quite favorably with calculated theoretical values as is shown in the following table:

TABLE II

Synthesis of Polyformals Partially Hydroxy-Terminated Comparison of Theoretical and Found Composition

| Run No. | Charge | | | | Yield [2] | Molecular Weight ($\overline{Mn}$) | | meq. OH/g | | OH Groups per Molecule | |
|---|---|---|---|---|---|---|---|---|---|---|---|
| | Thiodi-glycol moles | Formal-dehyde moles | 2-ethyl-hexanol moles | Catalyst [1] % by wt. | % by wt. | Theoretical | Found | Theoretical | Found | Theoretical | Found |
| 13 | 3.5 | 3.5 | 1.0 | 0.166 | 85 | 600 | 560 | 1.67 | 2.33 | 1 | 1.3 |
| 14 | " | " | " | " | 94 | " | 465 | " | 2.45 | " | 1.14 |
| 15 | " | " | " | 0.33 | 89 | " | 635 | " | 1.91 | " | 1.2 |
| 16 | " | " | " | 0.33 | 95 | " | 495 | " | 2.25 | " | 1.1 |
| 17 | " | " | " | 0.67 | 96 | " | 620 | " | 1.70 | " | 1.1 |
| 18 | " | " | " | 0.67 | 82 | " | 690 | " | 1.29 | " | 0.9 |
| 19 | " | " | " | 0.67 | 90 | " | 685 | " | 1.31 | " | 0.9 |
| 20 | " | " | " | 1.0 | 94 | " | 690 | " | 1.19 | " | 0.8 |
| 21 | " | " | " | 1.0 | 92 | " | 710 | " | 1.13 | " | 0.8 |
| 22 | 5.0 | 5.0 | " | 0.33 | 98 | 810 | 590 | 1.24 | 2.0 | " | 1.18 |
| 23 | " | " | " | 0.67 | 83 | " | 1,110 | " | 0.64 | " | 0.71 |
| 24 | " | " | " | 0.67 | 93 | " | 690 | " | 1.07 | " | 0.81 |

[1] p-Toluene sulfonic acid.
[2] Based on theoretical maximum yield after removal of all water generated in the condensation reaction.

All of the foregoing products were very hydrophobic liquids, light in color and low to medium in viscosity. Small proportions of the crude reaction products produced in this example were found to be extractible with water, resulting in the following change in properties of the products from which the water-extractible material was removed:

TABLE III
Water Extraction of Partially Hydroxy-Terminated Polyformals

| Run No. | Molecular Wt. ($\overline{Mn}$) Crude | $H_2O$-extracted | meq. OH/g Crude | $H_2O$-extracted |
|---|---|---|---|---|
| 15 | 635 | 690 | 1.91 | 1.57 |
| 17 | 620 | 690 | 1.70 | 1.36 |
| 22 | 590 | 740 | 2.0 | 1.45 |

EXAMPLE IV

In this and the following example additional polyformals were made in the presence of 2-ethylhexanol, utilizing the procedure of Example I, by which the resultant compositions were endcapped with the monoalcohol to a higher degree than in the previous example.

| Thiodiglycol | 244 g (2 moles) |
|---|---|
| Paraformaldehyde | 90 g (3 moles $CH_2O$) |
| 2-Ethylhexanol | 260 g (2 moles) |
| p-Toluene sulfonic acid | 3 g (0.5% wt., total charge) |

All the reactants were charged together and heated for 3 hours at 103° C, after which stripping was initiated to remove reaction water by raising the temperature of the reaction mixture to 140° C. After stripping for 1 hour, a vacuum was applied to remove all remaining higher boiling volatiles. The reaction mixture was then cooled. The light colored reaction product was insoluble in water; it contained only 0.5 meq. OH/g and had an average of 0.27 hydroxy groups per molecule. The molecular weight ($\overline{Mn}$) was 540.

In view of the higher degree of endcapping, the principal reaction mechanism was as follows:

n(HO-CH$_2$-CH$_2$-S-CH$_2$-CH$_2$-OH) + (n+1)CH$_2$O + 2 iso-C$_8$H$_{17}$OH → C$_8$H$_{17}$-O-CH$_2$-O(CH$_2$-CH$_2$-S-CH$_2$CH$_2$-O-CH$_2$-O)$_n$C$_8$H$_{17}$ + (n+1)H$_2$O wherein, within the context of the general formula, the symbolized groups have the following composition and values:

| Group | Composition |
|---|---|
| $R_1$ | 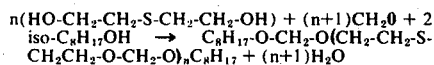 |
| $R_2$ | 2-ethylhexyl |
| $R_3$ | 2-ethylhexyl |
| A | —CH$_2$—CH$_2$—S—CH$_2$—CH$_2$— |

EXAMPLE V

The same experiment as in Example IV was carried out, except that 6 grams of catalyst were employed. The resulting liquid product was insoluble in water; it contained only 0.44 meq. OH/g with an average of 0.24 hydroxy end groups per molecule. It was observed that the higher catalyst concentration seemed to improve the efficiency of endcapping in that a somewhat higher percentage of the 2-ethylhexanol was reacted than in the previous example (88% wt. versus 86.5%).

EXAMPLE VI

This example illustrates the preparation of a series of polyformals, partially endcapped with longer alkyl groups derived from n-dodecanol-1.

Employing a constant molar charge ratio of 3.5/3.5/1 thiodiglycol/formaldehyde/n-dodecanol-1, a series of water-immiscible plasticizers partially endcapped with n-dodecanol-1 was prepared in accordance with the general procedure of Example I, except for certain process variations as indicated. The reaction mechanism was as follows:

n(HO-CH$_2$-CH$_2$-S-CH$_2$-CH$_2$-OH) + nCH$_2$O + nC$_{12}$H$_{25}$OH → C$_{12}$H$_{25}$-O-CH$_2$O(CH$_2$-CH$_2$-S-CH$_2$-CH$_2$-O-CH$_2$-O)$_{n-1}$CH$_2$-CH$_2$-S-CH$_2$-CH$_2$-OH +nH$_2$O

In reference to the general formula for the products of invention, the symbolized groups thereof had the following compositions:

| Group | Composition |
|---|---|
| $R_1$ | 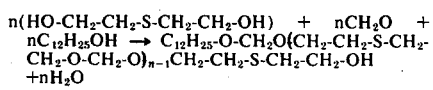 |
| $R_2$ | —CH$_2$—CH$_2$—S—CH$_2$—CH$_2$—OH |
| $R_3$ | n-dodecyl |
| A | —CH$_2$—CH$_2$—S—CH$_2$—CH$_2$— |

Process variations included: (a) catalyst level (0.3 and 0.6% by wt. p-toluene sulfonic acid) and (b) mode of n-dodecanol addition (initial addition of total n-dodecanol charge and two modes of incremental addition). Total reaction time was about 7 hours throughout, at temperatures of between 105° and 145° C, the higher temperature being used toward the end of the reaction, during which vacuum was applied to remove volatiles. Yields and compositions correspond well with theoretical values as is shown in the following table:

TABLE IV
Synthesis of Polyformal Plasticizers Partially Terminated with n-Dodecanol-1

| Run No. | Catalyst (% by wt.) | n-Dodecanol Mode of Addition | Reaction Product [4] Yield (% of Theory) | $\overline{Mn}$ | meq. OH/g | OH Groups/ Molecule |
|---|---|---|---|---|---|---|
| 25 | 0.3 | (1) | 97 | 560 | 1.97 | 1.1 |
| 26 | 0.3 | (1) | 99 | 645 | 1.42 | 0.9 |
| 27 | 0.6 | (1) | 97 | 675 | 1.49 | 1.0 |
| 28 | 0.6 | (1) | 97 | 675 | 1.70 | 1.1 |
| 29 | 0.6 | (2) | — | 575 | 2.10 | 1.2 |

TABLE IV-continued

Synthesis of Polyformal Plasticizers Partially Terminated with n-Dodecanol-1

| Run No. | Catalyst (% by wt.) | n-Dodecanol Mode of Addition | Yield (% of Theory) | Mn | meq. OH/g | OH Groups/ Molecule |
|---|---|---|---|---|---|---|
| 30 | 0.6 | (2) | — | 690 | 0.94 | 0.65 |
| 31 | 0.6 | (3) | 96 | 725 | 1.47 | 1.1 |
| 32 | 0.6 | (3) | 97 | 660 | 1.90 | 1.2 |

(1) Together with all other reactants.
(2) 3 increments, 45 minutes apart, beginning 1 hour after thiodiglycol and formaldehyde charged.
(3) Dropwise over 90 minute period, beginning 1 hour after thiodiglycol and formaldehyde charged.
(4) Theoretical Values: $\overline{Mn}$ = 655; meq. OH/g = 1.53; OH groups/molecule = 1.

EXAMPLE VII

An additional series of polymerizations was performed according to Example VI, to prepare water-immiscible polyformal plasticizers mono-endcapped with n-dodecanol-1 utilizing a constant molar charge ratio of 5/5/1 thiodiglycol/formaldehyde/n-dodecanol-1. In this series, variations in the catalyst level and the mode of adding the mono-alcohol were observed. The results of these experiments, as shown in Table V below, indicated no significant difference due to the different mode of addition of the endcapping agent. However, higher catalyst levels produced products with molecular weights and hydroxy values closer to theoretical.

TABLE V

Synthesis of Polyformal Plasticizers Partially Terminated With n-Dodecanol-1

| Run No. | Catalyst (% by wt.) | Mono-alcohol Mode of Addition | Yield (% of Theory) | $\overline{Mn}$ | meq. OH/g | OH Groups/ Molecule |
|---|---|---|---|---|---|---|
| 33 | 0.5 | (1) | 95 | 705 | 1.64 | 1.2 |
| 34 | 0.9 | (1) | 95 | 845 | 1.05 | 0.9 |
| 35 | 0.5 | (2) | 95 | 660 | 1.58 | 1.0 |
| 36 | 0.5 | (3) | 95 | 705 | 1.54 | 1.1 |
| 37 | 0.9 | (2) | 94 | 805 | 1.1 | 0.9 |
| 38 | 0.9 | (3) | 92 | 825 | 0.96 | 0.8 |

(1) Total addition with other reactants.
(2) Dropwise addition over 1.5 hour period, beginning 1 hour after thiodiglycol and formaldehyde charged.
(3) 3 increments, 45 minutes apart, beginning 1 hour after thiodiglycol and formaldehyde charged.
(4) Theoretical Values: $\overline{Mn}$ = 856; meq. OH/g = 1.17; OH groups/molecule = 1.

EXAMPLE VIII

Two further experimental polymerizations were performed to produce polyformals having an average of 25% of the terminal groups endcapped with n-dodecanol-1, i.e. comprising about a 50/50 mixture of completely hydroxy-terminated polymers and mono-endcapped polymers. Utilizing the general procedure outlined in Example I, the reactions were run at 110°–135° C for 6–7 hours. The reactant charge for each polymerization was as follows:

| Run No. 39 | Thiodiglycol | 518 g (4.25 moles) |
| | Paraformaldehyde | 115 g (3.82 moles CH$_2$O) |
| | n-Dodecanol-1 | 93 g (0.5 mole) |
| | p-Toluene sulfonic acid | 4 g (0.55% by wt.) |
| Run No. 40 | Thiodiglycol | 395 g (3.25 moles) |
| | Paraformaldehyde | 85 g (2.83 moles CH$_2$O) |
| | n-Dodecanol-1 | 93 g (0.5 mole) |
| | p-Toluene sulfonic acid | 3 g (0.52% by wt.) |

In Run No. 39, 96% of theoretical yield was obtained and the product contained 2.25 meq. OH/g, as compared to a theoretical value of 2.28. In Run No. 40, 96% of theoretical yield was obtained and the product contained 2.67 meq. OH/g, as compared with a theoretical value of 2.88. Both products were light colored liquids and were insoluble in water.

EXAMPLE IX

In this example, monobutyl glycols were employed as endcapping agents in the synthesis of polyformals utilizing the following reactant charges:

| Run No. 41 | Thiodiglycol | 122 g (1 mole) |
| | Paraformaldehyde | 30 g (1 mole CH$_2$O) |
| | Mono-n-butyl-diglycol (Ektasolve-DB*) | 39 g (0.25 mole) |
| | p-Toluene sulfonic acid | 1 g (0.5% wt.) |
| Run No. 42 | Thiodiglycol | 122 g (1 mole) |
| | Paraformaldehyde | 30 g (1 mole CH$_2$O) |
| | Mono-isobutyl-diglycol (Ektasolve-DIB*) | 39 g (0.25 mole) |
| | p-Toluene sulfonic acid | 1 g (0.5% wt.) |
| Run No. 43 | Thiodiglycol | 73 g (ca. 0.5 mole) |
| | Paraformaldehyde | 24 g (0.8 mole CH$_2$O) |
| | Mono-n-butyl-glycol (Ektasolve-EB*) | 47 g (0.4 mole) |
| | p-Toluene sulfonic acid | 0.7 g (0.7% wt.) |
| Run No. 44 | Thiodiglycol | 73 g (ca. 0.6 mole) |
| | Paraformaldehyde | 24 g (0.9 mole CH$_2$O) |
| | Mono-isobutyl-glycol (Edtasolve-EIB*) | 47 g (0.4 mole) |
| | p-Toluene sulfonic acid | 0.7 g (0.7% wt.) |

*Products sold by Eastman Chemical Co.

All reactants were charged at the same time and the reaction was carried out at 107°–112° C for 4 hours, after which the temperature was raised to 143° C under vacuum, to remove all reaction water and other volatiles.

The products from Runs 41 and 42 were predominately mono-endcapped with the monovalent residue of mono-n-butyl and mono-isobutyl diglycols, respectively. The products from Runs 43 and 44 were substantially di-endcapped with the monovalent residue of the respective butylglycols. The properties of each of the products, all of which were light colored, water-insoluble liquids, were then compared with theoretical values. The results are set forth in Table VI below.

TABLE VI

Preparation of Polyformals Terminated With Butyl Glycols

| Run No. | Yield (% of Theory) | Molecular Weight ($\overline{Mn}$) | | meq. OH/g | | OH Groups per Molecule | |
|---|---|---|---|---|---|---|---|
| | | Theoretical | Found | Theoretical | Found | Theoretical | Found |
| 41 | 95 | 692 | 615 | 1.45 | 1.64 | 1 | 1.0 |
| 42 | 88 | 692 | 700 | 1.45 | 1.43 | 1 | 1.0 |
| 43 | 82 | 650 | 600 | 0 | 0.87 | 0 | 0.52 |
| 44 | 78 | 650 | 755 | 0 | 0.51 | 0 | 0.39 |

The data for Runs 43 and 44 indicate that endcapping was about 74% and over 80% complete, respectively.

EXAMPLE X

A polymerization reaction was performed in which a polyformal was prepared with terminal end groups derived from 2-ethyl-isohexanol. The procedure employed was basically the same as in Example I, using the following charge of reactants:

| | |
|---|---|
| Thiodiglycol | 85 g (0.7 mole) |
| Paraformaldehyde | 21 g (0.7 mole CH$_2$O) |
| 2-Ethyl-isohexanol | 26 g (0.2 mole) |
| p-Toluene sulfonic acid | 0.9 g (0.8% wt.) |

A light colored water-insoluble liquid product was obtained at a 92% wt. yield. Molecular weight ($\overline{Mn}$) was 760 and the product contained 1.1 hydroxy groups per molecule.

EXAMPLE XI

In this example, dodecylbenzene sulfonic acid was compared with p-toluene sulfonic acid as catalyst for the synthesis of a thiodiglycol polyformal partially endcapped with mixed C$_{12}$/C$_{13}$ alkyl mono-alcohols (sold by Shell Chemical Co. under tradename of Neodal 23). The reactant charges were as follows:

| Run No. | 45 | 46 | |
|---|---|---|---|
| Charge | | | |
| Thiodiglycol | 447 g | 447 g | (3.67 moles) |
| Paraformaldehyde | 100 g | 100 g | (3.3 moles CH$_2$O) |
| Mixed C$_{12}$/C$_{13}$ alkyl mono-alcohols (Neodal 23) | 131 g | 131 g | (0.67 mole) |
| Dodecyl benzene sulfonic acid (DBSA) | 5.6 g | — | (0.7% wt.) |
| p-Toluene sulfonic acid (TSA) | — | 3.5 g | (0.5% wt.) |

Using the same procedure for Runs 45 and 46, all reactants were charged into a two liter, 3 necked flask having a jacket for steam heating and equipped with a reflux condenser, gas inlet and outlet and stirring means. The apparatus was purged with nitrogen and nitrogen was also passed to the vapor outlet of the reflux condenser to prevent air from entering the reaction flask. The reaction mixture was heated with stirring to 95°–99° C. After about one-half hour, the cloudy reaction mixture cleared up, and a small amount of water condensed in the upper part of the apparatus indicating complete depolymerization of the paraformaldehyde and the onset of the principal reaction. After 4 hours of reaction at 98°–99° C, the reaction mixture was cooled at 72° and a vacuum applied to the reactor system to remove water and other volatiles. After vacuum stripping for 3 hours at temperatures of 95° to 99° C, heating was discontinued and the reaction mixture allowed to cool under vacuum.

Over 600 g of clear liquid product were obtained from the DBSA-catalyzed reaction, having a molecular weight ($\overline{Mn}$) of 514 and containing 2.40 meq. OH/g, which indicates 38.5% endcapping. About the same amount of clear liquid product was obtained from the TSA-catalyzed reaction having a molecular weight ($\overline{Mn}$) of 482 and containing 2.65 meq. OH/g, which indicates 36% endcapping with alkyl groups. Thus, the two catalysts were quite comparable in effectiveness.

EXAMPLE XII

The method of making the products of the invention is quite flexible, as is shown by the following synthesis in which a partially endcapped product was produced using a mixture of thiadiol and diol as well as a mixture of monoalcohols for endcapping.

The following listed reactants were charged together and heated to 75°–120° C for 4 hours, after which the volatiles were removed therefrom by stripping (Run No. 47):

| | |
|---|---|
| Thiodiglycol | 61 g (0.5 mole) |
| Ethylene glycol | 31 g (0.5 mole) |
| p-Formaldehyde | 36 g (1.7 moles CH$_2$O) |
| 2-Ethylhexanol | 19 g (0.15 mole) |
| n-Octanol | 7 g (0.05 mole) |
| p-Toluene sulfonic acid | 0.2 g (0.16% wt.) |

The resultant polymeric product was a very light yellowish water-insoluble liquid. 114 g of clear product was obtained having a $\overline{Mn}$ of 570 and contained 2.7 meq. OH/g and 13.5% sulfur. This amount of sulfur indicates a copolymer of thiodiglycol and ethylene glycol was formed.

It should here be noted that the diol charge was comprised of a mixture of vicinal diol and non-vicinal thiadiol, ethylene glycol and thiodiglycol, respectively. While vicinal diols may be used, as here, in admixture with nonvicinal thiadiols to form complex polyformals, they may not be used by themselves, since, under the reaction conditions, they would form cyclic formals. In the case of ethylene glycol, 1,3-dioxolane is formed. It should further be noted that the product from this reaction is a complex mixture of polymers endcapped with either or both 2-ethylhexyl and n-octyl groups.

EXAMPLE XIII

When a thiodiglycol/formaldehyde/2-ethylhexanol polyformal product, made in pilot plant scale equipment in all essential respects by the procedure of Example III, was admixed with separate quantities of 1,3 and 6 normal sulfuric acid and heated for several hours over a steam bath, no hydrolysis took place and the samples were all free of either formaldehyde or alcohol. Only when the partially endcapped product was treated with 57% hydroiodic acid for 30 minutes at 160° C, was some hydrolytic cleavage of the polymer detectable. This shows the exceptional stability of the product toward strong acids.

EXAMPLE XIV

An unendcapped thiodiglycol/formaldehyde polymer was made in accordance with the procedure of Example I having the following properties:

| | |
|---|---|
| $\overline{Mn}$ | 735 |
| meq. OH/g | 2.4 |

In an attempt to sulfate the polymer, it was treated with chlorosulfonic acid ($ClSO_3H$) at 30°–50° C for 2 hours and then further reacted at pH 0–1 for several hours. No change in the properties of the product could be detected which indicates the stability of the product toward acid hydrolysis.

The products of the invention are also stable at alkaline pH by nature of their chemical structure. Thus, the products are particularly advantageous, since they can be used over a wide range of pH values, in both aqueous and non-aqueous systems. The water-soluble polyformals disclosed in the prior art are less stable and therefore unsuitable at low pH values, i.e. less than 5.

The products have also been found to have outstanding thermal stability, which in inert atmospheres is comparable to polyethers, such as polyethylene glycols. Moreover, in oxidative atmospheres the products are comparable to polyesters. Under oxidative conditions, it would be expected that the sulfur-containing products would form intermediate sulfoxides and sulfones. This property makes the thiapolyformals useful as synergistic antioxidants in rubber compounds.

EXAMPLE XV

The following examples illustrate the remarkable utility of the invention products as plasticizers for rubbers.

Six separate samples of a butadiene/acrylonitrile (74/26) rubber containing 3 parts per hundred rubber (phr) of a 1:1:1 blend of three commercial antioxidants (Flectol-H, Monsanto; Antioxidant-MB, Mobay; Agerite-Stalite, R. T. Vanderbilt) were placed on a conventional two-roll mixing mill and compounded for curing by the addition of the following additional components:

TABLE VII

| | Rubber Compounded With Hydroxy-Terminated Polyformals of Thiodiglycol (Non-Endcapped) | | | | | |
|---|---|---|---|---|---|---|
| Milled Component | Amount (basis 100 parts by wt. (polymer) | | | | | |
| Compound No. | 1 | 2 | 3 | 4 | Control A | Control B |
| Vulcanization agent (sulfur) | 0.4 | 0.4 | 0.4 | 0.4 | 0.4 | 0.4 |
| Accelerator (2 Ethylcadmate (3.5 Altax* | 5.5 | 5.5 | 5.5 | 5.5 | 5.5 | 5.5 |
| Activator (10 Maglite D (MgO) (3.5 Cadmium oxide | 13.5 | 13.5 | 13.5 | 13.5 | 13.5 | 13.5 |
| Promoter (1.5 Stearic Acid) | 1.5 | 1.5 | 1.5 | 1.5 | 1.5 | 1.5 |
| Reinforcing agent (SRF-black N-762) | 50 | 50 | 50 | 50 | 50 | 50 |
| Plasticizer | 8 (1) | 8 (2) | 8 (3) | 8 (4) | 8 (5) | None |

| | | meq. OH/q |
|---|---|---|
| (1) | Product from Run No. 1, Example I | 4.4 |
| (2) | Product from Run No. 2, Example I | 3.3 |
| (3) | Product from Run No. 3, Example I | 3.3 |
| (4) | Product from Run No. 4, Example I | 2.1 |
| (5) | Commercially available polyether poly-thioether plasticizer (Plastikator OT-Bayer) | 0.1 |

*Benzothiazyl disulfide

Each of the above compounded rubbers was oven cured at 163° C until 100% cure was obtained as measured on a Monsanto Rheograph. Samples of each of the cured rubbers were then formed into Type C dumbbells and the tensile and elongation properties of each dumbbell was determined on one-half of each of the dumbbell samples. The remaining dumbbells were aged in an air-circulating oven for 72 hours at 149° C at the conclusion of which the cooled samples were likewise measured as to their tensile and elongation properties.

TABLE VIII

Effect of Oxidative Heat Aging Upon Plasticized Nitrile Rubbers

| Compound No. | 1 | 2 | 3 | 4 | Control A | Control B |
|---|---|---|---|---|---|---|
| $T_b$-initial [1] | 2639 | 2581 | 2550 | 2461 | 2547 | 2774 |
| $T_b$-aged [1] | 2555 | 2450 | 2625 | 2500 | 2390 | 2320 |
| % Loss (Gain) | 3.2 | 5.1 | (2.9) | (1.6) | 6.2 | 16 |
| $E_b$-initial [2] | 498 | 494 | 488 | 458 | 528 | 396 |
| $E_b$-aged [2] | 413 | 405 | 435 | 375 | 278 | 198 |
| % Loss | 17 | 18 | 11 | 18 | 47 | 50 |
| Hardness-initial [3] | 60 | 60 | 60 | 61 | 61 | 68 |
| Hardness-aged [3] | 71 | 70 | 70 | 71 | 72 | 78 |
| Gain | 11 | 10 | 10 | 10 | 11 | 10 |
| Compression Set-aged | 65 | 64 | 64 | 64 | 71 | 67 |
| Plasticizer Loss, % wt. | 23 | 15 | 16 | 9 | 46 | — |

[1] Tb denotes tensile strength at break as measured on an Instron tensile tester per ASTM Test Procedure D-412-68.
[2] Eb denotes the % elongation at break as measured on Instron tensile tester per ASTM Test Procedure D-412-68.
[3] Per ASTM Test Procedure D-2240-68.

The rubber containing no plasticizer (Control B), of course, underwent the highest loss in aged tensile strength (16%). Used of the commercially available polyether polythioether plasticizer reduced the loss in aged tensile strength to only 6%. However, the plasticizers of the invention reduced loss of tensile strength upon aging even further and in two instances actually improved the tensile strength of the aged rubber.

As would be expected, all the plasticizers increased the elongation properties of the nitrile rubber. However, the rubber containing the commercially available plasticizer incurred almost a 50% loss in elongation upon aging, whereas the rubber containing the plasticizer of the invention incurred a maximum loss of only 18% in elongation upon aging.

Again, as would be expected, each of the plasticizers produced a decrease in hardness due to plasticization of the rubber. Surprisingly, however, the rubbers plasticized with the products of the invention had a desirably lower compression set, whereas the commercially available plasticizer caused a substantial increase in compression set of the aged rubber. At least part of the superiority of the invention products may be attributed to the fact that less plasticizer was lost during aging, which indicates better compatibility as well as lower volatility.

The foregoing results indicate that the hydroxy-terminated plasticizer of the invention are effective plasticizers for rubber. The plasticizers also impart oxidative heat resistance, while not adversely affecting the other physical properties of the rubber.

EXAMPLE XVI

Two additional series of nitrile rubbers were formulated in precisely the same manner as in Example XV utilizing the partially endcapped plasticizers from Run Nos. 17 and 21 (Example III, Table II) and the water extracted product from Run No. 17 (Example III, Table III). Control samples were also prepared in accordance with Example XV using 8 parts of polythioether plasticizer (Plastikator OH-Bayer). The results were as follows:

TABLE IX

Effect of Oxidative Heat Aging Upon Nitrile Rubber Plasticized with 2-Ethylhexanol Endcapped Plasticizers

| Compound No. | 5 | 6 | 7 | Control |
|---|---|---|---|---|
| (Run No.) | 17 | 17 Extrd. | 21 | — |
| $T_b$-initial | 2376 | 2285 | 2303 | 2284 |
| $T_b$-aged | 2388 | 2337 | 2280 | 2049 |
| % Loss (Gain) | (0.3) | (2.3) | 1.0 | 10.3 |
| $E_b$-initial | 518 | 492 | 500 | 512 |
| $E_b$-aged | 413 | 388 | 375 | 323 |
| % Loss | 20 | 21 | 25 | 37 |
| Hardness-initial | 63 | 62 | 63 | 62 |
| Hardness-aged | 71 | 70 | 71 | 72 |
| Gain | 8 | 8 | 8 | 10 |
| Plasticizer Loss, % wt. | 23 | 21 | 15 | 49 |

Again it was found that the products of the invention, when used to plasticize rubber, were superior in their ability to reduce loss of rubber properties upon aging. In particular, the plasticizers of the invention produced much lower loss of tensile strength upon aging and in some instances even produced a slightly increased tensile strength. Likewise, elongation at break after aging was substantially higher with the plasticizers of the invention as compared with the competitive plasticizer, which itself has outstanding plasticizing action for heat aged rubbers.

It will be noted, too, that the water extraction of the products of the invention, as shown in the data for compound 17 Extrd. did not greatly alter the performance of the product. By comparison of the data in this example with Example XV, it can be observed that higher hydroxy content seems generally advantageous for heat resistance. In addition, those plasticizers having higher molecular weight showed lower weight losses during aging.

EXAMPLE XVII

A series of nitrile rubber compounds were made utilizing thiodiglycol/formaldehyde polyformals partially endcapped to various degrees with n-dodecanol. The plasticizers were synthesized in accordance with the procedure of Examples VI and VII and were compounded into the rubber in the manner of Example XV. The compounded rubbers were then compared with the same rubber compounded with the above-referred commercial polythioether plasticizer (control). However, in this series of tests, the compounds, in addition to aging under oxidative conditions (oven aging), were aged under more mildly oxidative conditions (test tube aging). The latter type of aging was done by heating each dumbbell in an open 200 ml. test tube by which no circulation of air to the sample could take place. The properties of this series of compounds were as follows:

Moreover, it is seen from the above that the plasticizers having the higher hydroxy content contribute most to heat resistance. However, increasing molecular weight of the plasticizers also influences heat resistance positively.

EXAMPLE XVIII

In this example, a series of rubbers was prepared utilizing the same compounding and sample preparation procedures as in Example XVII and utilizing the

TABLE X

Effects of Heat Aging Upon Nitrile Rubbers Plasticized with n-Dodecanol-Endcapped Plasticizer

| Compound No. | 8 | 9 | 10 | 11 | Control |
|---|---|---|---|---|---|
| $T_b$-initial | 2265 | 2251 | 2182 | 2258 | 2284 |
| $T_b$-aged | 2232 | 2292 | 2257 | 2342 | 2049 |
| % Loss (Gain) | 1.5 | (1.8) | (3.4) | (3.7) | 5.9 |
| $T_b$-aged [1] | 2107 | 2086 | 2227 | 2265 | 1999 |
| % Loss (Gain) | 7.0 | 7.3 | (2.1) | (0.3) | 12.5 |
| $E_b$-initial | 480 | 504 | 492 | 502 | 512 |
| $E_b$-aged | 368 | 380 | 390 | 418 | 323 |
| % Loss | 23 | 25 | 21 | 17 | 37 |
| $E_b$-aged [2] | 370 | 370 | 410 | 440 | 330 |
| % Loss | 23 | 25 | 19 | 12 | 36 |
| Hardness initial | 63 | 62 | 63 | 62 | 62 |
| Hardness aged | 70 | 70 | 70 | 70 | 72 |
| Hardness [3] | 70 | 69 | 68 | 68 | 68 |
| Plasticizer Loss, % wt., Oven aged | 12.5 | 20 | 21 | 27 | 49 |
| Plasticizer Properties | | | | | |
| Molecular Wt. ($\overline{M_n}$) | 900 | 725 | 570 | 510 | — |
| meq. OH/g | 1.07 | 1.47 | 1.62 | 2.19 | — |
| OH Groups/molecule | 0.96 | 1.07 | 0.92 | 1.12 | — |

[1] $T_b$, aged in test tube.
[2] $E_b$, aged in test tube.
[3] Hardness, aged in test tube.

As would be expected from the previous two examples, the products of the invention imparted quite remarkable retention of the tensile and elongation properties to the rubbers during aging. Losses in tensile at break were quite low and in some instances the rubber exhibited an increase in aged tensile strength.

The elongation of the test-tube aged and oven-aged rubbers containing the plasticizers of the present invention was distinctly superior to the control rubber containing the commercially available plasticizer.

above-referred polyether polythioether and eight other commercially available plasticizers in separate samples from the same rubber batch. By way of indirect comparison with the products of the invention, two separate quantities of a similar rubber were identically compounded with a thiodiglycol/formaldehyde polyformal partially endcapped with n-decanol (Compound No. 11, and Control ex Table X) and polyether polythioether as a control. The results of these comparisons were as follows:

TABLE XI

Comparison of Various Commercially Available Plasticizers for the Plasticization of Heat-aged Rubbers

| Plasticizer | Invention | Polyether Polythio- (Control)[1] | Dioctyl Phthalate | Polysulfide Liquid Polymer[2] | Triphenyl Phosphate | Tetrahydro furfural Oleate | High M.Wt. Polyester[3] | Tricresyl Phosphate | High M.Wt. Polyester[4] | Dioctyl Adipate | Polyether Polythioether[1] |
|---|---|---|---|---|---|---|---|---|---|---|---|
| $T_b$-initial | 2258 | 2284 | 1841 | 1884 | 1211 | 1791 | 1557 | 1675 | 1653 | 1900 | 1875 |
| $T_b$-aged | 2342 | 2049 | 1920 | 1732 | 1619 | 1585 | 1628 | 1744 | 1605 | 1508 | 1638 |
| % Loss (Gain) | (3.7) | 10 | (4.3) | 8.1 | (34) | 12 | (4.6) | (4.4) | 2.9 | 21 | 13 |
| $E_b$-initial | 502 | 512 | 345 | 284 | 342 | 368 | 290 | 315 | 293 | 363 | 350 |
| $E_b$-aged | 418 | 323 | 210 | 168 | 225 | 215 | 213 | 220 | 225 | 198 | 249 |
| % Loss | 17 | 37 | 39 | 41 | 34 | 42 | 27 | 30 | 23 | 46 | 29 |
| Hardness-initial | 62 | 62 | 63 | 70 | 63 | 61 | 63 | 64 | 64 | 61 | 62 |
| Hardness-aged | 70 | 72 | 70 | 74 | 72 | 72 | 73 | 69 | 71 | 72 | 66 |
| Gain | 8 | 10 | 7 | 4 | 9 | 11 | 10 | 5 | 7 | 11 | 4 |
| Plasticizer Loss | 27 | 49 | 69 | 75 | 63 | 60 | None | 43 | None | 82 | 33 |

TABLE XI-continued

Comparison of Various Commercially Available Plasticizers for the Plasticization of Heat-aged Rubbers

| Plasticizer | Invention | Polyether Poly- thio- (Control)[1] | Dioctyl Phthalate | Polysulfide Liquid Polymer[2] | Tri- phenyl Phos- phate | Tetra- hydro furfural Oleate | High M.Wt. Poly- ester[3] | Tri- cresyl Phos- phate | High M.Wt. Poly- ester[4] | Dioctyl Adipate | Polyether Polythio- ether[1] |
|---|---|---|---|---|---|---|---|---|---|---|---|
| % wt. | | | | | | | | | | | |

[1] Plastikator OT, tradename of Farbenfabriken Bayer, A.G., Leverkusen, W. Germany
[2] Thiokol LP-3, tradename of Thiokol Corp., Trenton, N.J.
[3] Paraplex G-25, tradename of Rohm & Haas Co., Philadelphia, Pa.
[4] Plastolein 9789, tradename of Emery Industries, Cincinnati, Ohio From the foregoing, it can be seen that the thiodiglycol polyformal of this invention together with the polyether-polythioether (control 1) exhibited both the highest initial tensile strength and elongation of the entire series. Upon heat aging the rubber containing the product of this invention was about as good as or better than any one of the rubber containing the other plasticizers with respect to retention of tensile strength. However, none of the other plasticizers was as effective as the product of the invention in retaining the elongation properties of the aged rubber. Furthermore, it is apparent that the final elongation (after heat aging) of the rubber plasticized with the polyformal is by far the highest of the entire series. The hardness after heat aging of the vulcanizate containing the plasticizer of the invention was one of the lowest.

EXAMPLE XIX

Using the general procedure of Example I, a partially endcapped polythiaalkylene formal was made utilizing the following reactant charge:

| | |
|---|---|
| Thiodiglycol | 62.0 lbs. |
| Paraformaldehyde | 15.8 lbs. |
| Mixed C$_{12-13}$ alkyl monoalcohols (Neodol-23) | 20.2 lbs. |
| p-toluene sulfonic acid | 2.0 lbs. |

The resulting product, which was produced at 92% of theoretical yield, had the following properties:

| | |
|---|---|
| $\overline{M_n}$ | 1,030 |
| meq. OH/g | 0.58 |
| OH groups/molecule | 0.6 |

The above described water-insoluble liquid product was then compounded into a polychloroprene rubber (50 neoprene WM-1/50 neoprene WHV-100) on a conventional two-roll mixing mill according to the following formulation:

| | | |
|---|---|---|
| Vulcanization agent (sulfur) | 1.0 | |
| Accelerator (dodecylmercaptan) | 1.5 | |
| Activator (10 phr zinc oxide 4 phr MgO) | 14.0 | Parts by wt., basis 100 parts by wt. dry rubber (phr) |
| Promotor (stearic acid) | 0.5 | |
| Reinforcing agents (20 phr SRF Black 80 phr Dixie Clay) | 100.0 | |
| Plasticizer of this Examples | 20.0 | |
| Antioxidant (1 phr Aranox (Uniroyal Chemical) 4 phr Octamine (Uniroyal Chemical) | 5.0 | |

The above compounded rubber was over cured at 163° C until 100% cure was obtained as measured on a Monsanto Rheograph. Samples of the cured rubbers were then formed and the tensile and elongation properties of the rubbers determined.

TABLE XII

Effect of oxidative Heat Aging Upon Plasticized Polychloroprene Rubber Samples

| Compound No. | 12 |
|---|---|
| | (Average) |
| $T_b$ - initial | 1767 |
| $T_b$ - aged | 1570 |
| % Loss (Gain) | 11 |
| $E_b$ - initial | 568 |
| $E_b$ - aged | 433 |
| % Loss | 24 |
| Hardness - initial | 63 |
| - aged | 74 |
| - gain | 11 |
| Compression Set - aged | 71 |

The above data show clearly that the plasticizers of the invention are comparably effective for polychloroprene as well as nitrile rubbers.

What is claimed is:

1. A new water-insoluble polymeric composition having polythiaformal linkages therein, of the formula:

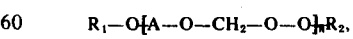

$$R_1-O[A-O-CH_2-O-O]_nR_2,$$

wherein $R_1$ is selected from the group consisting of hydrogen and the group $R_3-O-CH_2-$; $R_2$ and $R_3$ are independently selected from the group consisting of hydrogen and monovalent residues of mono-alcohols and thiadiols, said residues of mono-alcohols being present in the statistical average polymer chain at least to about 20 mole percent of the terminal groups; A is the divalent residue of thiadiol having at least 4 carbon atoms; $n$ is an integer from 2 through 40; said thiadiols selected from the group consisting of primary thiaalkylenes, oxa-thiaalkylenes, polythiaalkylenes, and mixtures thereof; and said mono-alcohols selected from the group consisting of primary alkyls, thiaalkyls, oxaalkyls, aralkyls, alkenyls, and mixtures thereof.

2. The composition of claim 1 in which the divalent residues of thiadiol are a primary thiaalkylene having from 4 to 35 carbon atoms.

3. The composition of claim 1 in which the monovalent residues of mono-alcohols are primary alkyl having from 2 to 35 carbon atoms.

4. The composition of claim 1 in which the divalent residues of thiadiol are primary thiaalkylenes having 4 to 35 carbon atoms and the monovalent residues of mono-alcohols are primary alkyls having from 2 to 35 carbon atoms.

5. The composition of claim 1 which is the liquid phase reaction product of primary thiadiol, formaldehyde, and mono-alcohol.

6. The composition of claim 5 in which primary thiadiol is thiodiglycol.

7. The composition of claim 5 in which the mono-alcohol is 2-ethylhexanol-1.

8. The composition of claim 5 in which the primary thiadiol is thiodiglycol and the mono-alcohol is 2-ethylhexanol-1.

9. The composition of claim 5 in which the mono-alcohol is selected from the group consisting of primary dodecanol and mixed primary fatty alcohols containing 12 to 13 carbon atoms.

10. The composition of claim 1 in which A is the divalent residue of a mixture of the said thiadiol and nonsulfur-containing polyols having from 2 40 carbon atoms, said polyol residue being not more than 60 mole percent of the divalent thiadiol residue.

* * * * *